United States Patent [19]

McFadden et al.

[11] 4,153,791

[45] May 8, 1979

[54] 3-CARBOXY-4 HYDROXYPHENYLTHIOACETMORPHOLIDE

[75] Inventors: Arthur R. McFadden, East Brunswick; Richard C. Allen, Flemington; Thomas B. K. Lee, Whitehouse Station, all of N.J.

[73] Assignee: American Hoechst Corporation, Bridgewater, N.J.

[21] Appl. No.: 939,267

[22] Filed: Sep. 5, 1978

Related U.S. Application Data

[62] Division of Ser. No. 843,482, Oct. 19, 1977, Pat. No. 4,118,401.

[51] Int. Cl.² .................................... C07D 295/18
[52] U.S. Cl. .................................... 544/161
[58] Field of Search .................................... 544/161

[56] References Cited

U.S. PATENT DOCUMENTS 4,118,401  10/1978  McFadden et al. ........... 544/161

FOREIGN PATENT DOCUMENTS 1409411  7/1965  France ........... 544/161

*Primary Examiner*—Natalie Trousof
*Assistant Examiner*—R. W. Ramsuer
*Attorney, Agent, or Firm*—Curtis, Morris & Safford

[57] ABSTRACT

A process, and intermediates for the preparation of 6,11-dihydro-11-oxodibenz[b,e]oxepin-2-acetic acid are described. The acid possesses antiinflammatory and analgesic activity.

1 Claim, No Drawings

3-CARBOXY-4-HYDROXYPHENYLTHIOACETMORPHOLIDE

This is a division, of application Ser. No. 843,482, filed Oct. 19, 1977. now Pat. No. 4,118,401.

This invention relates to an improved method for preparing 6,11-dihydro-11-oxodibenz[b,e]oxepin-2-acetic acid, a valuable pharmaceutical agent possessing antiinflammatory and analgesic activity and to several intermediates therefor.

To the best of our knowledge neither the method of this invention, nor the intermediates prepared, have heretofore been described or suggested. The most closely related prior methods for preparing 6,11-dihydro-11-oxodibenz[b,e]oxepin-2-acetic acid involve the reaction:

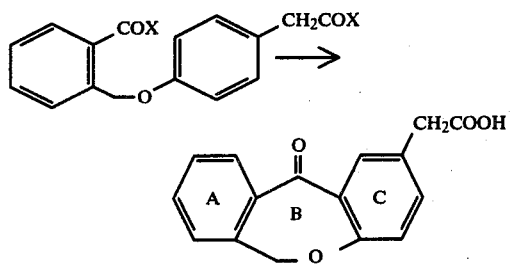

in which X is OH or a group convertible into OH. Such a process involves cyclization to the ring activated by the oxygen (e.g. to the ring which becomes the "C" ring of Compound II).

Prior methods specific for the preparation of 6,11-dihydro-11-oxodibenz[b,e]oxepin-2-acetic acid which utilize this reaction include:

Herbst et al., U.S. patent application Ser. No. 806,513, filed June 14, 1977, which discloses cyclization of a diacid halide under modified Friedel-Crafts conditions.

Helsley et al., U.S. patent application Ser. No. 459,774, filed Apr. 10, 1974 and Ueno et al., Belgian Pat. No. 818,055, which disclose the cyclization of a dicarboxylic acid by treatment with a dehydrating or condensing medium under specific conditions.

A more remote prior art method is disclosed in Japanese Pat. No. 52,017,486 published Feb. 9, 1977. This method involves ring closure by necleophilic displacement resulting in ether formation, e.g.

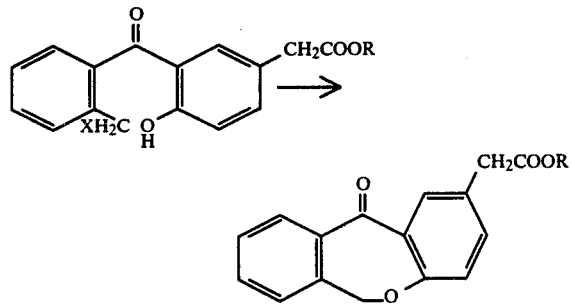

wherein X is halogen and R is hydrogen or lower alkyl.

The method of the present invention relates to the cyclization of 4-benzyloxy-3-carboxyphenylacetic acid, a novel intermediate:

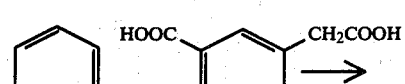

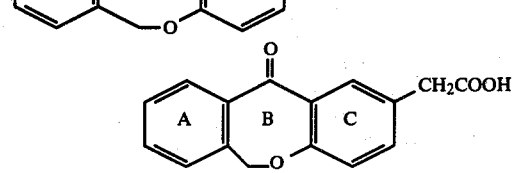

Ring formation in this process involves cyclization to the ring which is not activated by the oxygen (e.g. to the ring which becomes the "A" ring in Compound II). This represents a cyclization considered more difficult than the prior art processes.

This cyclization can be achieved by treatment of the intermediate (Compound III) with a large excess of a dehydrating agent such as polyphosphoric acid, ethanol-phosphorus pentoxide or sulfuric acid at a temperature of about 70°–200° C. Additionally, a solvent such as tetramethylene sulfone or acetic acid may be employed.

Alternatively, the 4-benzyloxy-3-carboxyphenylacetic acid can be converted to corresponding 4-benzyloxy-3-chlorocarbonylphenylacetyl chloride with an agent such as thionyl chloride which is then cyclized to the desired acid under Friedel Crafts type conditions. A preferred catalyst is aluminum chloride. A preferred solvent is methylene chloride/nitromethane.

The aforesaid novel intermediate is prepared through a multi-step process also producing two other novel compounds. This multi-step process is as follows:

A. 5-acetylsalicylic acid is reacted with sulfur and morpholine according to the conditions of the Willgerodt Reaction to obtain 3-carboxy-4-hydroxyphenylthioacetmorpholide, a novel compound.

B. The 3-carboxy-4-hydroxyphenylthioacetmorpholide is treated with a benzylhalide such as benzylbromide in the presence of a mild base, such as potassium carbonate, in a suitable solvent under reflux conditions to produce 4-benzyloxy-3-(benzyloxycarbonyl)phenylthioacetmorpholide, another novel intermediate.

C. The 4-benzyloxy-3-(benzyloxycarbonyl)phenylthioacetmorpholide is treated with aqueous potassium hydroxide at reflux conditions to produce the aforementioned immediate precursor, 4-benzyloxy-3-carboxyphenylacetic acid.

EXAMPLE

A. A mixture of 30.0 g of 5-acetylsalicylic acid, 9.0 g of sulfur and 54 ml of morpholine is maintained at 140°–145° C. for 19 hours to effect a dark viscous oil. The oil is decanted into 100 ml of ice water and the aqueous mixture is extracted with ether prior to being acidified with ice cold concentrated hydrochloric acid. The acidified aqueous phase is also extracted with ether and combined with the previous ether extracts. The combined ether extracts are sequentially washed with water, dried, filtered and concentrated leaving a dark brown solid which is washed successively with chloroform and methanol. The solid is recrystallized from acetonitrile to provide pale yellow crystals, mp 196°–198° C., of 3-carboxy-4-hydroxyphenylthioacetmorpholide.

Analysis

Calculated for $C_{13}H_{15}NSO_4$: 55.50%C; 5.37%H; 4.98%N. Found: 55.34%C; 5.40%H; 4.91%N.

B. A mixture of 1.0 g of 3-carboxy-4-hydroxyphenylthioacetmorpholide, 1.4 g of benzylbromide and 4.0 g of potassium carbonate in 50 ml of butanone is refluxed for 18 hours. The reaction mixture is permitted to cool before being filtered. The filtrate is successively diluted with ether, washed with water, dried, filtered and concentrated to leave an orange oil. The oil is eluted on a silica gel column with chloroform leaving 4-benzyloxy-3-(benzyloxycarbonyl)phenylthioacetmorpholide as a clear oil.

Analysis:
Calculated for $C_{27}H_{27}NOS_4$: 70.25%C; 5.90%H. Found: 69.47%C; 5.99%H.

C. A mixture of 7.0 g of 4-benzyloxy-3-(benzyloxycarbonyl)phenylthioacetmorpholide, 15.0 g of potassium hydroxide and 60 ml of water is refluxed for 16 hours. The refluxed mixture is permitted to cool, before being extracted with ether. The remaining aqueous phase is acidified with ice cold concentrated hydrochloric acid which is also extracted with ether. The acidic ether extracts are combined and then successively dried, filtered and concentrated leaving a yellow solid. The solid is treated with hot ether before being treated with hot benzene to effect a colorless solid which is recrystallized from acetonitrile to leave colorless crystals, mp 143°–145° C. of 4-benzyloxy-3-carboxyphenylacetic acid.

Analysis:
Calculated for $C_{16}H_{14}O_5$: 67.13%C; 4.93%H. Found: 66.88%C; 4.90%H.

D. A sample of 4-benzyloxy-3-carboxyphenylacetic acid is treated with an amount greater than the stoichiometric amount of polyphosphoric acid over a two hour span at 150°–200° C. The reaction mixture is permitted to cool and is then quenched with water, leaving a solid. The solid is collected by suction filtration, washed with water and then recrystallized from isopropyl alcohol to leave colorless crystals, mp 137°–138° C., of 6,11-dihydro-11-oxodibenz[b,e]oxepin-2-acetic acid.

E. A sample of 4-benzyloxy-3-carboxyphenylacetic acid is treated with an excess of thionyl chloride at reflux for 2 hours. The excess thionyl chloride is removed in vacuo and the remaining 4-benzyloxy-3-(chlorocarbonyl)phenylacetyl chloride is dissolved in methylene chloride-nitromethane and treated with an equivalent amount of aluminum chloride. The reaction mixture is stirred several hours at room temperature, refluxed for two hours and quenched with dilute hydrochloric acid. The layers are separated, the organic phase dried and evaporated in vacuo to a residue which, on crystallization from isopropyl alcohol yields 6,11-dihydro-11-oxodibenz[b,e]oxepin-2-acetic acid, mp 137°–138° C.

The claim:
1. 3-carboxy-4-hydroxyphenylthioacetmorpholide.
* * * * *